(12) United States Patent
Shiffer

(10) Patent No.: US 7,112,873 B2
(45) Date of Patent: Sep. 26, 2006

(54) FLIP CHIP METAL BONDING TO PLASTIC LEADFRAME

(75) Inventor: Stephen R. Shiffer, Pearl City, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/934,813

(22) Filed: Sep. 3, 2004

(65) Prior Publication Data

US 2006/0049529 A1    Mar. 9, 2006

(51) Int. Cl.
*H01L 23/495* (2006.01)
*H01L 23/48* (2006.01)

(52) U.S. Cl. .................. 257/677; 257/778; 257/782

(58) Field of Classification Search ............... 257/677, 257/671
See application file for complete search history.

(56) References Cited

U.S. PATENT DOCUMENTS

| | | | | |
|---|---|---|---|---|
| 3,670,394 A | * | 6/1972 | Daniels et al. | 228/110.1 |
| 3,778,530 A | * | 12/1973 | Reimann | 174/261 |
| 3,781,596 A | * | 12/1973 | Galli et al. | 361/751 |
| 4,151,543 A | * | 4/1979 | Hayakawa et al. | 257/668 |
| 4,447,857 A | * | 5/1984 | Marks et al. | 361/739 |
| 5,563,442 A | | 10/1996 | Mahulikar et al. | 257/666 |
| 5,744,383 A | | 4/1998 | Fritz | 438/111 |
| 6,006,427 A | | 12/1999 | Zak | 29/480 |
| 6,022,583 A | | 2/2000 | Falcone et al. | 427/96 |
| 6,274,650 B1 | | 8/2001 | Cui | 523/457 |
| 6,378,759 B1 | | 4/2002 | Ho et al. | 228/180.21 |
| 6,489,229 B1 | | 12/2002 | Sheridan et al. | 438/614 |
| 6,492,197 B1 | | 12/2002 | Rinne | 438/108 |
| 6,657,298 B1 | * | 12/2003 | Glenn | 257/730 |
| 6,707,135 B1 | | 3/2004 | Madrid | 257/666 |
| 2002/0182773 A1 | | 12/2002 | Su et al. | 438/111 |
| 2003/0057541 A1 | * | 3/2003 | Betori | 257/690 |

FOREIGN PATENT DOCUMENTS

EP                930651 A1 *  7/1999

* cited by examiner

*Primary Examiner*—Lex H. Malsawma
(74) *Attorney, Agent, or Firm*—Matthew F. Lambrinos; Kermit D. Lopez

(57) ABSTRACT

A plastic substrate can be provided and thereafter a plurality of metal-to-metal connections can be ultrasonically bonded to the plastic substrate. One or more dies and a plurality of conductive components thereof can then be respectively connected to the metal-to-metal connections in order to provide a plastic leadframe package structure that includes electronic circuitry thereon. The plurality of conductive components can be configured as discrete components, while the die itself can be configured as a Flip Chip On Plastic Leadframe component. By utilizing plastic as the basis for a substrate, ultrasonic bonding of the metal-to-metal connections, a complex substrate formed from plastic can provide a structure, particularly a plastic leadframe structure, that allows for the use of parts and components that are much less expensive than presently utilized parts and components.

13 Claims, 3 Drawing Sheets

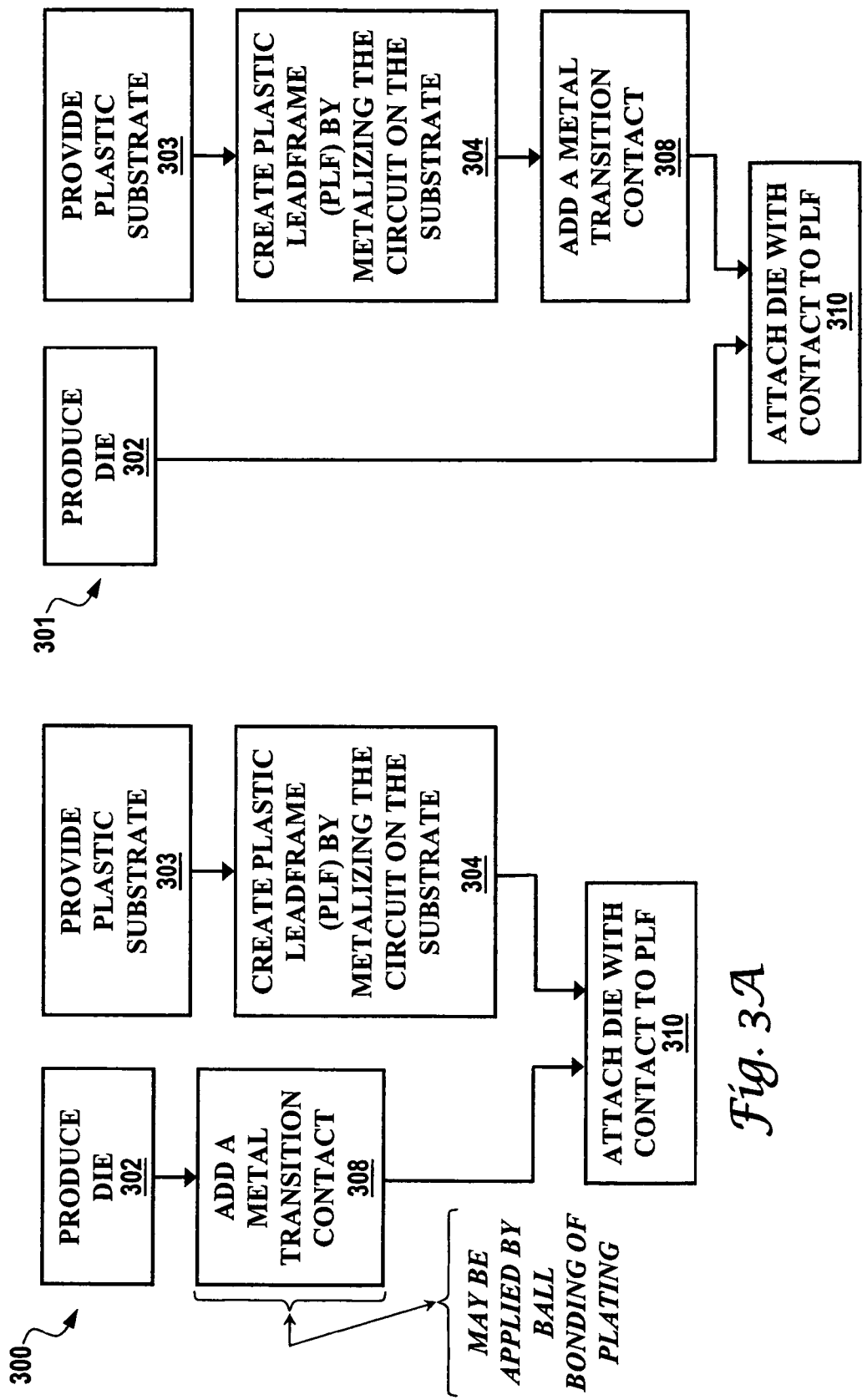

FLIP CHIP METAL BONDING TO PLASTIC LEADFRAME

TECHNICAL FIELD

Embodiments are generally related to integrated circuit manufacturing and assembly processes, including the packaging of electrical components. Embodiments also relate to Flip Chip On Board (FCOB) and conductive plastic trace assembly methods and systems. Embodiments also relate to ultrasonic bonding and leadframe structures.

BACKGROUND OF THE INVENTION

Most electronic packages, which include sensors connected to input/output devices thereof, utilize leadframes, a PCB, or combinations thereof. Such electronic packages generally require that conductors and/or insulators connect from a sensing element to the outside of the package for a customer to properly interface with the device. Leadframes provide customized configurations in which a designer can create many packages in order to meet a customer's overall need. Unfortunately, all of this customization must link in some electrical means to create a device. Common methods of connecting to leadframes including wire bonding and soldering techniques. Both of these connecting methods require that the leadframe be plated. Common plating material for wire bonding involves the use of gold, while tin is often utilized for soldering.

A number of complications are involved in the use of leadframes. For example, leadframes require cleaning following stamping and prior to plating in order to remove excessive oils and contaminates. Leadframes also function as a conductor and require an insulator to allow a usable electronic connection. Leadframes additionally require a significant capital investment to produce the conductor. The ability of a leadframe to be manipulated into a desired package configuration is very limited because the method of production chosen typically involves stamping. The simplest leadframe would be flat and straight. Any deviation from the simple design requires significant effort to ensure that angles and bends are precise for not only the package configuration, but also interface with the overmold process. It can thus be appreciated that the use of leadframes presents a number of assembly and manufacturing issues.

An alternative to leadframes is the PCB (Printed Circuit Board), which has become an economical means for producing circuitry utilizing copper foil, fiberglass, and resin to create the insulated conductor. This method maximizes the efficiency of the conductor when compared to the leadframe, because the conductor material requirement comes closer to meeting the electrical requirements required by the circuit. Yet, PCB issues include the cost of the board when the size becomes large. In addition, the conductor is merely flat.

Also, a requirement exists to provide an interconnect to the PCB in order to interface with the customer's I/O. Due to the standardization of PCBs, the designer must attempt to optimize the area within the panel. Additionally, routing may be required, not only to give the PCB dimensional size, but also to disconnect from the panel. Thus, the use of PCB components can result in a number of problems in component assembly and manufacturing, which may not in fact be superior the use of lead frames.

In creating small electronic components, such as sensor devices, for example, packing designs utilize metal conductors and/or leadframes to connect such devices to an input component, which is typically not cost-effective with respect to the overall assembly and manufacturing process. The solution to such cost issues touches many elements of the resulting component structure, such as material, labor and capital. A need thus exists for an assembly process, which overcomes these cost issues, while also providing the full capabilities of devices, such as PCB, leadframe and/or metal conductor components. It is believed that a solution to these problems lies in the combined use of Filp Chip On Board (FCOB), plastic substrate, and ultrasonic bonding techniques.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide an improved packaging assembly method and system.

It is another aspect of the present invention to provide for packaging assembly methods and systems involving the use of plastic substrates and ultrasonic bonding techniques.

The aforementioned aspects of the invention and other objectives and advantages can now be achieved as described herein. Packaging assembly methods and systems are disclosed. A plastic substrate can be provided and thereafter a plurality of metal-to-metal connections can be ultrasonically bonded to the plastic substrate. One or more dies and a plurality of conductive components thereof can then be respectively connected to the metal-to-metal connections in order to provide a plastic leadframe package structure that includes electronic circuitry thereon. The plurality of conductive components can be configured as discrete components, while the die itself can be configured as a Flip Chip On Board (FCOB) component. By utilizing plastic as the basis for a substrate and, ultrasonic bonding of the metal-to-metal connections, a complex substrate formed from plastic can provide a structure, particularly a plastic leadframe structure, that allows for the use of parts and components that are much less expensive than presently utilized parts and components.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 3(a) illustrates a high level flow chart of manufacturing operations, which can be implemented in accordance with one embodiment of the present invention;

FIG. 3(b) illustrates a high level flow chart of manufacturing operations, which can be implemented in accordance with an alternative embodiment of the present invention;

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figures 1, 2:
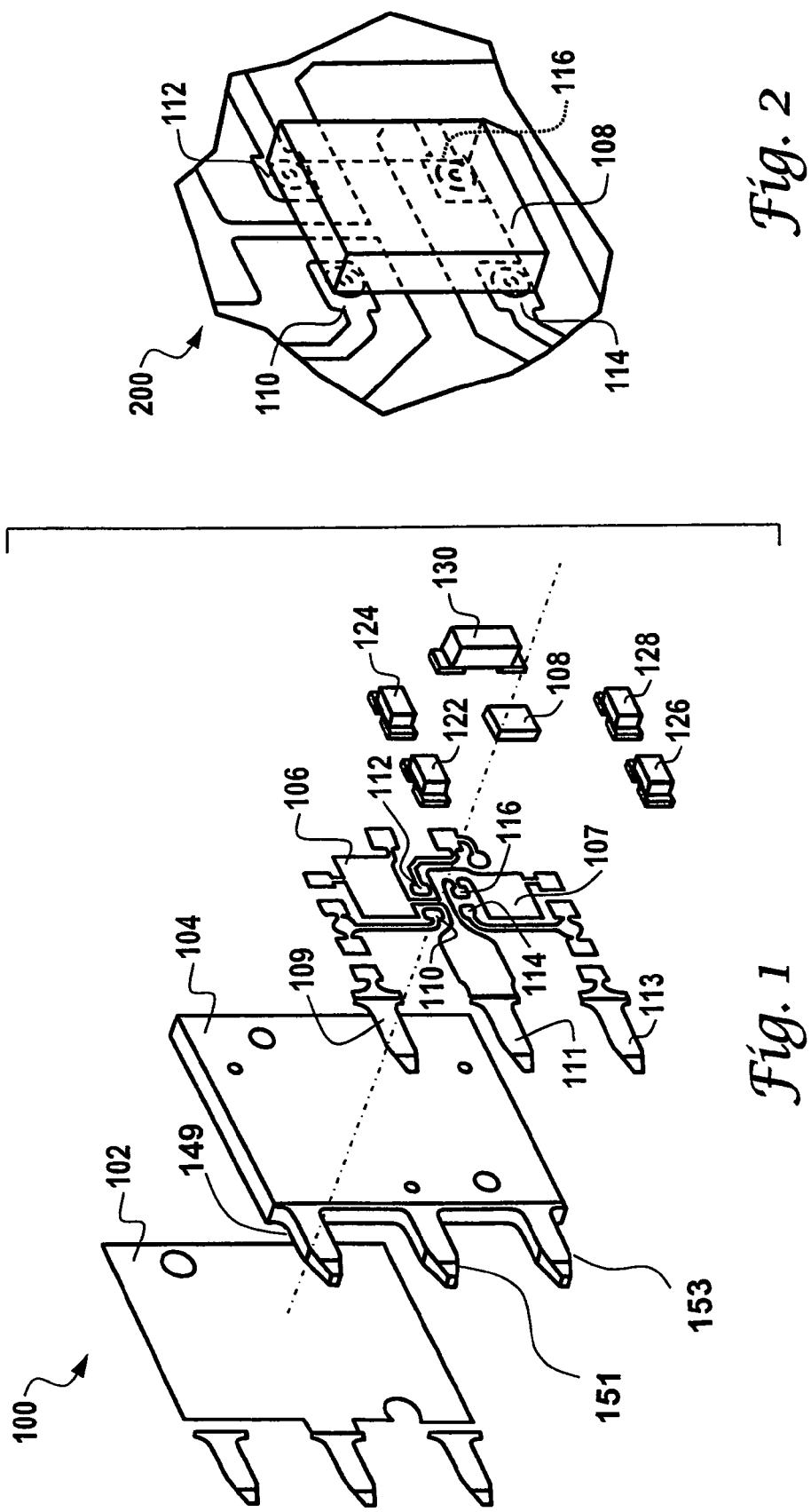
FIG. 1 illustrates an exploded view of a packaging assembly, which can be manufactured in accordance with an embodiment of the present invention.
FIG. 2 illustrates a section of the packaging assembly depicted in FIG. 1 as assembled, in accordance with an embodiment of the present invention.

FIG. 1 illustrates an exploded view of a packaging system or packaging assembly 100, which can be manufactured in accordance with an embodiment of the present invention. FIG. 2 illustrates a section 200 of the packaging assembly 100 depicted in FIG. 1 as assembled, in accordance with an embodiment of the present invention. Note that in FIGS. 1 and 2, identical or similar parts or elements are indicated by identical reference numerals. A plastic substrate 104 can initially be provided, which is located between a bottom portion 102 and top portions 106, 107, 109, 111, and 113.

Plastic substrate 104 can be subject to an ultrasonic bonding operation in which metal-to-metal connections (e.g., top portions 106, 107, 109, 111, and 113) are formed thereon. In this manner, plastic substrate 104 can function as a complex substrate that provides structure and electrical connections, while allowing for associated, but inexpensive parts. Plastic substrate 104 can function as a plastic insulator. Bottom portion 102 can be configured from any conductive metal, such as, for example, copper, nickel, and so forth. In the configuration of FIG. 1, bottom portion 102 can also be designed to function as an EMC shield. Plastic substrate 104 can form part of or a basis for a plastic leadframe. Plastic substrate 104 includes pin portions 149, 151,153 to which metal-to-metal connections 109,111,113 are respectively bonded to thereby form the plastic leadframe.

The plastic substrate 104 can function as part of packaging assembly 100 by connecting a die 108 to the plastic substrate 104 to thereby configure the resulting conductive plastic trace assembly to function as a combined printed circuit board and package structure that includes electronic circuitry thereon. Die 108 can be attached to plastic substrate 104 utilizing ultrasonic technology. Additional discrete components 122, 124, 126, 128, and 130 can also be connected to the plastic substrate 104 to create the conductive plastic trace assembly (i.e., packaging assembly 100). Discrete components 122, 124, 126, 128 and 130 can be implemented as conductive components, depending upon design considerations. Such a packaging assembly 100 additionally can include a plurality of conductive contacts 110, 112, 114, and 116 to which die 108 attaches.

Such a packaging assembly 100 can create new manufacturing opportunities by increasing speed and reducing capital expenses due to the incorporation of tooling points into the plastic. The use of such tooling points promotes the consistent and accurate manipulation, placement, and structuring of packaging assemblies. As a result, few components are involved. In addition, handling and joint inspection is eliminated. Plastic substrate 104 incorporates key elements for creating the packaging assembly 100 is important, including the structure, electronic circuitry and the metallization required for conduction and component interface.

FIG. 3(a) illustrates a high level flow chart 300 of manufacturing operations, which can be implemented in accordance with one embodiment of the present invention. FIG. 3(b), on the other hand, illustrates a high level flow chart 301 of manufacturing operations, which can be implemented in accordance with an alternative embodiment of the present invention. Note that in FIGS. 3(a) and 3(b), identical or similar parts or elements are generally indicated by identical reference numerals. The flow charts 300 and 301 are described and illustrated herein in order to depict alternative methodologies for flip chip metal bonding to a plastic leadframe.

As depicted at block 302 of FIG. 3(a), a die can be produced. Meanwhile, as illustrated at block 303, a plastic substrate can be provided, which then forms the plastic leadframe by building circuitry on the plastic as illustrated at block 304. The operation depicted at block 304 indicates that metalizing the circuit on the substrate can create the plastic lead frame. An example of such a plastic substrate is depicted in FIGS. 1–2 (i.e., see plastic substrate 104). As depicted at block 308 of FIGS. 3(a) and 3(b), a metal transition contact can be configured to the die or the Plastic Leadframe (PLF) by a ball bond, plating, of other means to obtain electrical connection and provide a mass to conform to the second substrate for physical and electrical attachment as illustrated at block 308 Finally, as depicted at block 310, a die can be attached to the plastic leadframe through the transition contact.

Note that in FIG. 3(a), the operation depicted at block 308 generally occurs following the operation depicted at block 302, and/or simultaneously with the operations depicted at blocks 303 and/or 304. The operation depicted at block 310 of FIG. 3(a) can therefore occur following processing of the operation depicted at block 308 and the operation depicted at block 304. On the other hand, as illustrated in FIG. 3(b), the operation depicted at block 310 generally occurs following the operation depicted at 308 and the operation depicted at block 302.

Figure 4D:
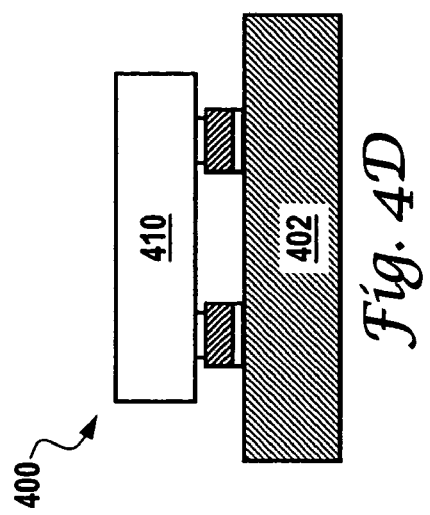
FIG. 4(d) illustrates a block diagram of a system, which can be configured in accordance with an alternative embodiment of the present invention.
Figure 4B:
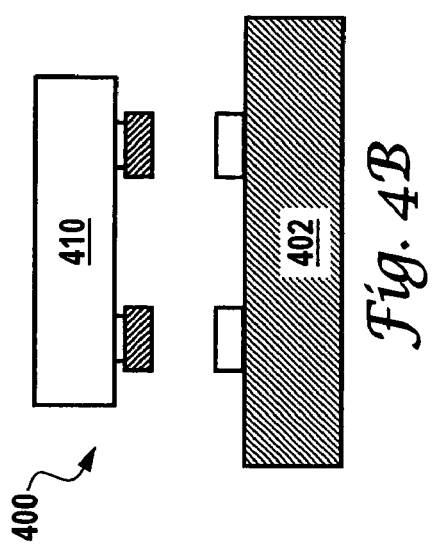
FIG. 4(b) illustrates a block diagram of a system, which can be configured in accordance with an alternative embodiment of the present invention.
Figure 4C:
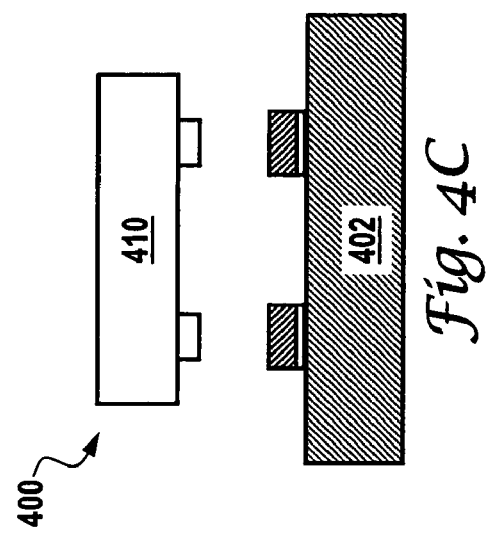
FIG. 4(c) illustrates a block diagram of a system, which can be configured in accordance with an alternative embodiment of the present invention.
Figure 4A:
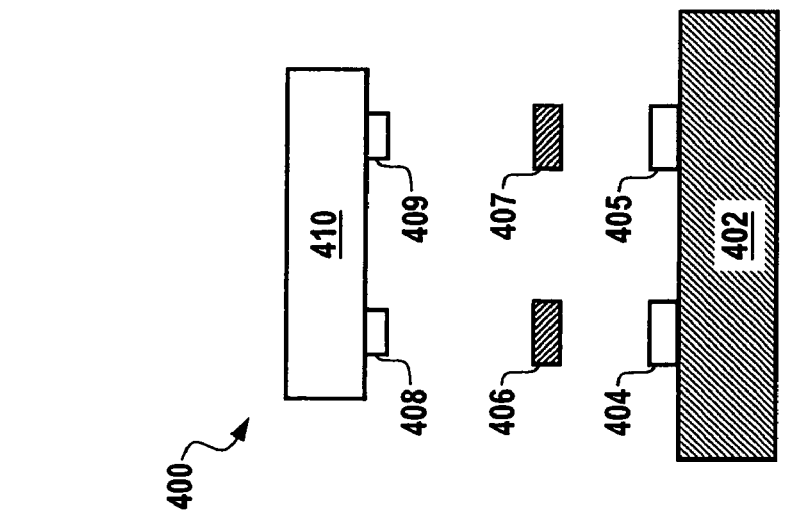
FIG. 4(a) illustrates a block diagram of a system, which can be configured in accordance with one embodiment of the present invention.

FIGS. 4(a)–4(b) illustrate a block diagram of a system 400, which can be configured in accordance with preferred or alternative embodiments of the present invention. Note that in FIGS. 4(a)–4(b), various configurations are illustrated, indicated how system 400 can be arranged. It can be appreciated that system 400 can be configured according to varying implementations. System 400 generally includes a plastic substrate 402, which is analogous to plastic substrate 104 of FIG. 1. The circuitry on the plastic is depicted as elements 404 and 405. A metal transition contact 406 and/or 407 can function as the bonding interface between the die 410 and the Plastic Leadframe (PLF).

Such a bonding interface can provide the physical and electrical connection to complete the circuit. Die contact pads 408 and 409 are also depicted in FIGS. 4(a)–4(b), which functions, as pad(s) on die 410 where the transition contacts 406 and/or 407 respectively attach on the die 410. As indicated by the methodologies of flow charts 300 and 301 of FIG. 3, it can be appreciated that there are at least two chief means for constructing such a device. The variations illustrated in FIGS. 4(a) to 4(b) are based on which substrate the metal transition contact will be attached first, i.e., the die or the Plastic Leadframe.

Typically, the final attachment can be accomplished by ultrasonic welding, but it can be appreciated that welding is not the only attachment means, which can be implemented. Ultrasonic bonding, which is sometimes also referred to as wedge bonding, is preferred because it is generally inexpensive, and under the proper conditions results in a very satisfactory connection. Additionally, ultrasonic bonding does not rely on external heating of associated parts. Wedge bonding utilizes a wedge-shaped bonding tool to press the wire strongly against the pad. High frequency acoustic energy without external heat can then be applied to the bonding tool, which vibrates the wire against a pad to form a mechanical and electrical bond between the wire and the pad. In the embodiments disclosed here, the plastic substrate can be utilized as the pad itself.

Note that die 410 can be configured as an Flip Chip On Plastic Leadframe (FCOPLF) component. A number of advantages can be obtained from configuring die 410 as an FCOPLF component, particularly one that connects to plastic substrate 402 via metal bonding technology. For example, the use of die 410 as an FCOPLF component promotes a reduction in the inductance associated with signal paths thereof due to the presence of shorter interconnects. This is a key factor in high-speed applications such as high-speed sensors, assuming that die 410 comprises a high-speed sensor die. The use of FCOPLF technology also promotes a high packaging density, so that the entire surface of die 410 can be utilized for interconnections and circuit routing rather than merely the edges thereof. Overall the resulting package size can be reduced through the use of FCOPLF technology.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The invention claimed is:

1. A packaging system, comprising:
  a plastic substrate having pin portions; and
  a plurality of metal-to-metal connections ultrasonically bonded to said plastic substrate including said pin portions to thereby form a plastic leadframe; and
  at least one die and a plurality of conductive components thereof respectively connected to said metal-to-metal connections in order to provide a plastic leadframe package structure that includes electronic circuitry thereon.

2. The system of claim 1 wherein said plurality of conductive components comprises discrete components.

3. The system of claim 1 wherein said die comprises a Flip Chip On Plastic Leadframe (FCOPLF) component.

4. The system of claim 1 wherein said metal-to-metal connections comprise a plurality of top portions located and connected to said plastic substrate including said pin portions.

5. The system of claim 4 wherein said plastic substrate is located adjacent to a bottom portion, such that said plastic substrate including said pin portions is sandwiched between said bottom portion and said plurality of top portions.

6. The system of claim 5 wherein said bottom portion comprises an EMC shield.

7. A packaging system, comprising:
  a plastic substrate having pin portions; and
  a plurality of metal-to-metal connections ultrasonically bonded directly to said plastic substrate including said pin portions to thereby form a plastic leadframe; and
  at least one Flip Chip On Plastic Leadframe (FCOPLF) component and a plurality of conductive components thereof respectively connected to said metal-to-metal connections in order to provide a plastic leadframe package structure that includes electronic circuitry thereon, said plurality of conductive components comprising discrete components.

8. The system of claim 7 wherein said at least one Flip Chip On Plastic Leadframe (FCOPLF) component comprises a sensor die.

9. The system of claim 7 wherein said plastic substrate functions as a printed circuit board (PCB).

10. The system of claim 7 wherein said metal-to-metal connections comprise a plurality of top portions located and connected to said plastic substrate including said pin portions.

11. The system of claim 10 wherein said plastic substrate is located adjacent to a bottom portion, such that said plastic substrate including said pin portions is sandwiched between said bottom portion and said plurality of top portions.

12. The system of claim 11 wherein said bottom portion comprises an EMC shield.

13. The system of claim 7 wherein said plastic substrate comprises a plastic insulating material.

* * * * *